United States Patent
Chuang et al.

(10) Patent No.: US 12,292,424 B2
(45) Date of Patent: May 6, 2025

(54) TWO-DIMENSIONAL LC-MS/MS SYSTEMS

(71) Applicant: Genzyme Corporation, Cambridge, MA (US)

(72) Inventors: Wei-Lien Chuang, Bridgewater, NJ (US); Felipe Gazos Lopes, Bridgewater, NJ (US); Joshua Pacheco, Bridgewater, NJ (US); Gerard Sanderink, Bridgewater, NJ (US)

(73) Assignee: Genzyme Corporation, Cambridge, MA (US)

( * ) Notice: Subject to any disclaimer, the term of this patent is extended or adjusted under 35 U.S.C. 154(b) by 384 days.

(21) Appl. No.: 17/615,291

(22) PCT Filed: May 29, 2020

(86) PCT No.: PCT/US2020/035231
§ 371 (c)(1),
(2) Date: Nov. 30, 2021

(87) PCT Pub. No.: WO2020/243502
PCT Pub. Date: Dec. 3, 2020

(65) Prior Publication Data
US 2022/0252559 A1 Aug. 11, 2022

Related U.S. Application Data

(60) Provisional application No. 62/855,636, filed on May 31, 2019.

(51) Int. Cl.
*G01N 30/46* (2006.01)
*B01D 15/18* (2006.01)
(Continued)

(52) U.S. Cl.
CPC ....... *G01N 30/468* (2013.01); *B01D 15/1878* (2013.01); *B01D 15/322* (2013.01);
(Continued)

(58) Field of Classification Search
CPC .... G01N 30/468; G01N 30/14; G01N 30/463; G01N 30/7233; G01N 2030/027;
(Continued)

(56) References Cited

U.S. PATENT DOCUMENTS 6,641,783 B1 * 11/2003 Pidgeon ............. G01N 30/7266
210/659
9,239,319 B2    1/2016 Sims et al.
(Continued)

FOREIGN PATENT DOCUMENTS

CN    109187822 A    1/2019
JP    2003-028849 A   1/2003
(Continued)

OTHER PUBLICATIONS

Afonso-Olivares et al. "Simplified solid-phase extraction procedure combined with liquidchromatography tandem-mass spectrometry for multiresidueassessment of pharmaceutical compounds in environmental liquidsamples" J Chromatogr. A (2017) 1487:54-63.
(Continued)

*Primary Examiner* — Natalie Huls
(74) *Attorney, Agent, or Firm* — Steptoe LLP; Z. Ying Li; Debashree Chatterjee

(57) ABSTRACT

The present invention relates to a novel analytical method for detecting one or more analytes in a source sample by continuous flow 2D LC-MS/MS using a single LC system.

18 Claims, 4 Drawing Sheets

(51) Int. Cl.
*B01D 15/32* (2006.01)
*G01N 30/02* (2006.01)
*G01N 30/14* (2006.01)
*G01N 30/72* (2006.01)

(52) U.S. Cl.
CPC ........... *B01D 15/325* (2013.01); *G01N 30/14* (2013.01); *G01N 30/463* (2013.01); *G01N 30/7233* (2013.01); *G01N 2030/027* (2013.01); *G01N 2405/08* (2013.01)

(58) Field of Classification Search
CPC ........... G01N 2405/08; G01N 33/6848; G01N 30/46; G01N 30/89; B01D 15/1878; B01D 15/322; B01D 15/325
See application file for complete search history.

(56) References Cited

U.S. PATENT DOCUMENTS

| | | | |
|---|---|---|---|
| 10,018,603 B2* | 7/2018 | Hyung | G01N 30/463 |
| 2006/0211849 A1 | 9/2006 | Kakehi | |
| 2007/0199874 A1 | 8/2007 | Masahito et al. | |
| 2008/0179251 A1* | 7/2008 | Davison | G01N 30/02 210/85 |
| 2009/0229352 A1* | 9/2009 | Kunz | C07C 233/87 562/433 |
| 2011/0097813 A1* | 4/2011 | Ito | G01N 30/463 210/659 |
| 2012/0240666 A1 | 9/2012 | Sims | |
| 2016/0054273 A1 | 2/2016 | Hyung et al. | |
| 2016/0109470 A1 | 4/2016 | Rolfs et al. | |
| 2016/0120958 A1 | 5/2016 | Chuang et al. | |
| 2016/0195502 A1* | 7/2016 | Mansani | G01N 30/7266 73/61.55 |
| 2016/0282369 A1* | 9/2016 | Cravatt | G01N 33/6842 |
| 2018/0306797 A1 | 10/2018 | Schaffer et al. | |
| 2019/0064128 A1 | 2/2019 | Dargy et al. | |
| 2021/0139868 A1* | 5/2021 | Scheidt-Puga | A61K 38/465 |

FOREIGN PATENT DOCUMENTS

| | | |
|---|---|---|
| JP | 2004-184215 A | 7/2004 |
| JP | 2008-309699 A | 12/2008 |
| JP | 2015-194363 A | 11/2015 |
| JP | 2017-173281 A | 9/2017 |
| KR | 10-0614099 B1 | 8/2006 |
| TW | 201736846 A | 10/2017 |
| TW | 201908731 A | 3/2019 |

OTHER PUBLICATIONS

Chuang et al. "A Simple, High-Throughput Method for Analysis of Ceramide, Glucosylceramide, and Ceramide Trihexoside in Dried Blood Spots by LC/MS/MS" Methods in Molecular Biology (2016) 1378: 263-72.
Dong et al. "Online and Automated Sample Extraction" Bioanalysis (2015) 7(17):2227-33.
Iguiniz et al. "Two-dimensional liquid chromatography in pharmaceutical analysis. Instrumental aspects, trends and applications." J Pharmaceut Biomed Anal. (2017) 145:482-503.
Iguiniz et al. "Quantitative aspects in on-line comprehensive two-dimensional liquid chromatography for pharmaceutical applications" Talanta (2019) 195:272-80.
Massood et al. "Quantitation of Multiple Sphingolipid Classes Using Normal and Reversed-Phase LC-ESI-MS/MS: Comparative Profiling of Two Cell Lines" Lipids (2012) 47:209-26.
Mokh et al. "Innovative SPE-LC-MS/MS technique for the assessment of 63 pharmaceuticals and the detection of antibiotic-resistant-bacteria: A case study natural water sources in Lebanon" Sci Total Environ. (2017) 609:830-41.
Pirok et al. "Recent Developments in Two-Dimensional Liquid Chromatography: Fundamental Improvements for Practical Applications" Anal Chem. (2019) 91:240-63.
Siu et al. "Fully automatable two-dimensional reversed-phase capillary liquid chromatography with online tandem mass spectrometry for shotgun proteomics", Proteomics (2011) 11: 2308-19.

* cited by examiner

Step 1:

LC System 1

Step 2:

LC System 1

Step 3:

LC System 1
NP= Normal Phase; RP= Reverse Phase

TWO-DIMENSIONAL LC-MS/MS SYSTEMS

CROSS-REFERENCE TO RELATED APPLICATIONS

This application is a national stage application under 35 U.S.C. § 371 of International Patent Application No. PCT/US2020/035231, filed May 29, 2020, which claims priority from U.S. Provisional Application No. 62/855,636, filed May 31, 2019. The disclosure of each of the aforementioned prior applications is incorporated herein by reference in its entirety.

BACKGROUND OF THE INVENTION

Liquid chromatography tandem mass spectrometry (LC-MS/MS) has emerged as a powerful technique for detecting and measuring a wide variety of analytes. It is quickly becoming the method of choice for accurate and precise quantitation of analytes from biological matrices. The major obstacle to LC-MS/MS analysis of samples from biological matrices is the presence of major matrix components, such as phospholipids, proteins, or nucleotides, that interfere with the identification and quantitation of analytes of interest present in these matrices (see, e.g., Carmical and Brown, Biomed. Chromatogr. A (2016) 30:710-20; and Massood et al., Lipids (2012) 47:209-26). A fundamental step in the development of bioanalytical methods requires the cleaning of samples to eliminate the major matrix contaminants prior to sample analysis. The methods used for sample cleaning are broadly categorized as either "offline," which refers to hands-on sample preparation procedures, or "online," which refers to sample preparation procedures performed by the liquid chromatography (LC) system (Afonso-Olivares et al., J Chromatogr. (2017) 1487:54-63; Mokh et al., Sci Total Environ. (2017) 609:830-41; and Dong et al., Bioanalysis (2015) 7:2227-33).

One of the most common offline sample cleanup methods is solid phase extraction (SPE), which is focused on eliminating matrix components and enriching analytes of interest using sample preparation cartridges (Vanol et al., Biomed. Chromatogr. (2017) 32:1-10; see also Afonso-Olivares, Mokh, and Dong, supra). An SPE extract containing analytes of interest is dried and reconstituted in another solvent system, which needs to be compatible with one-dimensional (1D) LC-MS/MS analysis. The process of drying and reconstituting samples in different solvent systems is called "solvent exchange" or "buffer exchange." This process is necessary because the solvent system used for SPE is typically incompatible with the solvent system used for 1D LC-MS/MS analysis. The solvent exchange process leads to sample loss and reduced reproducibility. Further, SPE cartridges are costly and the process is time-consuming. To eliminate the SPE step for sample cleanup, online two-dimensional (2D) LC-MS/MS has been developed. 2D LC-MS/MS uses a two-column system. The first column, often made with hydrophilic resin (normal phase chromatography), is used to eliminate major matrix contaminants prior to the introduction of samples of interest to the second column. The second column can be made of hydrophobic resin (reverse phase chromatography) and further resolves analytes of interest from other interfering molecules prior to introduction to the mass spectrometer (Iguiniz and Heinisch, J Pharmaceut Biomed Anal. (2017) 145:482-503; Ling et al., Biomed. Chromatogr. (2014) 28:1284-93; Pirok et al., Anal Chem. (2019) 91:240-63; and Iguiniz et al., Talanta. (2019) 195:272-80). Consequently, two different solvent systems are employed for traditional online 2D LC-MS/MS analytical methodologies. This requires a dedicated pump system for each column, as well as a multiple-port diverting valve to allow analyte transfer and solvent exchange. These requirements make traditional 2D LC-MS/MS methodologies very complex and expensive, outweighing the potential benefits of 2D LC-MS/MS. Most labs are not equipped to conduct this type of assay.

Thus, there remains a need for improved analytical methods that are precise and yet simple.

SUMMARY OF THE INVENTION

The present disclosure provides a novel 2D LC analytical method for analyzing one or more analytes in a source sample. The method comprises the steps of (a) extracting the one or more analytes from the source sample with an extraction solvent to obtain an extraction sample; (b) applying the extraction sample and a solvent system to a first liquid chromatography (LC) column with an LC system, wherein the first LC column is directly connected to a second LC column through a tube with a diverting valve; (c) setting the diverting valve to a first position at a first predetermined time such that the solvent effluent from the first LC column is directed to waste; (d) setting the diverting valve to a second position at a second predetermined time such that the solvent effluent from the first LC column enters the second LC column for further separation; (e) repeating steps (c) and (d) as needed; and (f) analyzing the chromatographically separated sample obtained from the second LC column. An LC system refers to an LC instrument with a pump system for inputting a solvent system to a LC column. By "directly" is meant that there is not a second LC system dedicated to the second column, and thus the present method utilizes only one LC system for both dimensions. In some embodiments, step (f) comprises using mass spectrometry (MS), such as tandem MS, to analyze the chromatographically separated sample obtained from the second LC column.

In some embodiments, the LC is a high performance liquid chromatography or ultra-high performance liquid chromatography. In some embodiments, the first LC column is a normal phase column and the second LC column is a reverse phase column, or vice versa.

In some embodiments, the solvent system for the 2D LC comprises one or more of methanol, acetonitrile, and water. In further embodiments, the solvent system further comprises ammonium acetate and/or formic acid.

By "solvent system" is meant the solvent mixture or combination used during an LC run for analyzing target analyte(s). During the run, the solvent composition may change (e.g., by varying the relative ratios of the components of the solvent mixture) but the change does not lead to a need to conduct solvent exchange on the sample when the sample travels from the first column to the second column. In some embodiments, the relative ratios of the components of the solvent system are varied during a sample run.

The source sample may be a biological sample, such as a tissue sample, serum, plasma, blood, dry blood spot, urine, saliva, sputum, tears, cerebrospinal fluid, seminal fluid, or feces. In some embodiments, the one or more analytes are protein(s), lipid(s), carbohydrate(s), nucleotides, metabolites, vitamins, hormones, or steroids.

In certain embodiments, the one or more analytes are ceramide and lyso-sphingomyelin, and the source sample is derived from the blood of a patient with acid sphingomyelinase deficiency. In further embodiments, the ceramide and lyso-sphingomyelin are extracted from a blood sample with an extraction solvent comprising 80% methanol (v/v), 15-20% acetonitrile (v/v), 0-5% water (v/v), 10 mM ammonium acetate, and 1% formic acid. In particular embodiments, the first LC column is a silica column and the second LC column is a C18 column (i.e., the resins of the columns are made of polymers with 18 carbons). In further embodiments, the solvent system comprises 0.5% trifluoroacetic acid.

In some embodiments, the solvent system applied to the first and second LC columns comprises 0-85% methanol (v/v), 0-15% acetonitrile (v/v), and 0-100% water (v/v). In further embodiments, the solvent system is made by mixing a first solvent comprising water and 0.5% trifluoroacetic acid, and a second solvent comprising 85% methanol (v/v), 15% acetonitrile (v/v), and 0.5% trifluoroacetic acid. In certain embodiments, the ratio of the first solvent to the second solvent is 70:30, 85:15, or 99:1.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

DETAILED DESCRIPTION OF THE INVENTION

Figure 1:
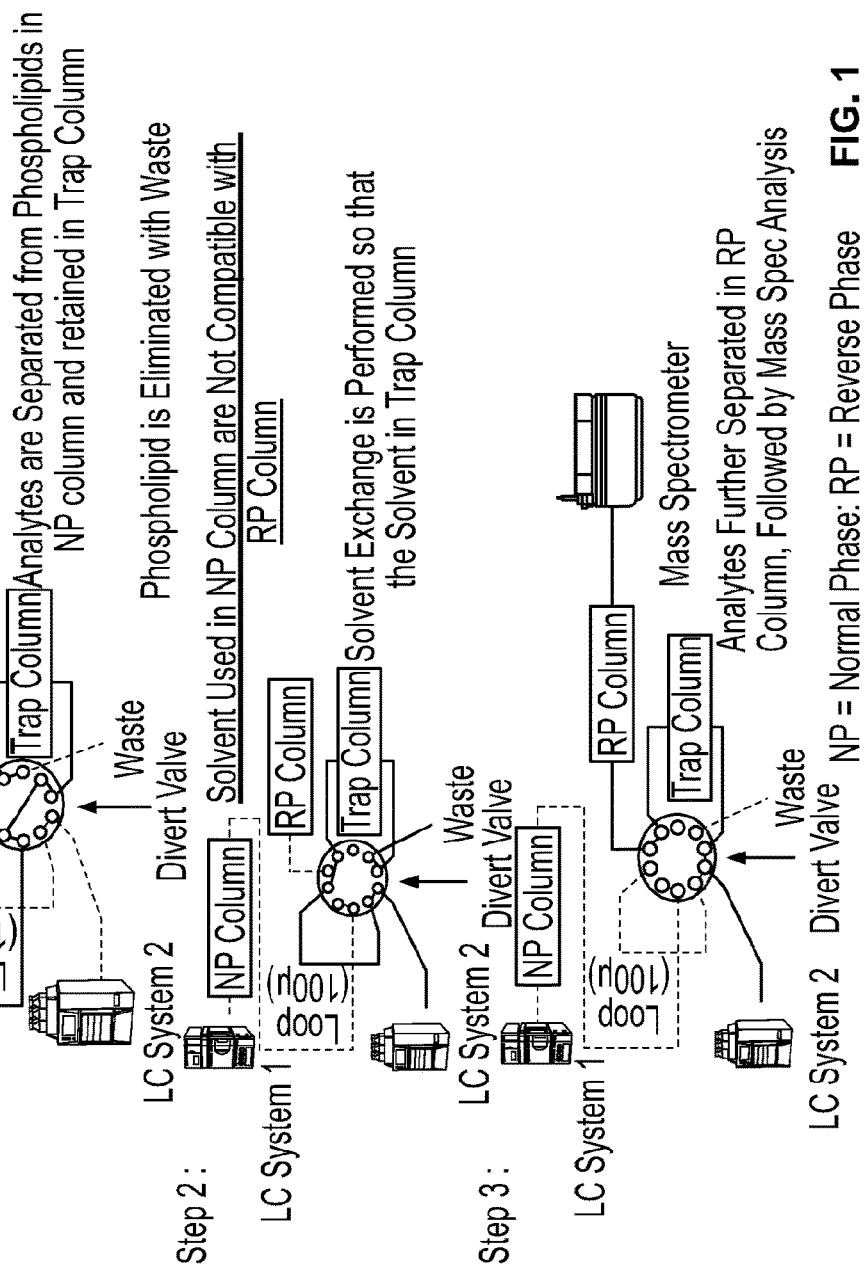
FIG. 1 is a schematic presentation shows the setup of traditional online 2D LC-MS/MS.
Figure 2:
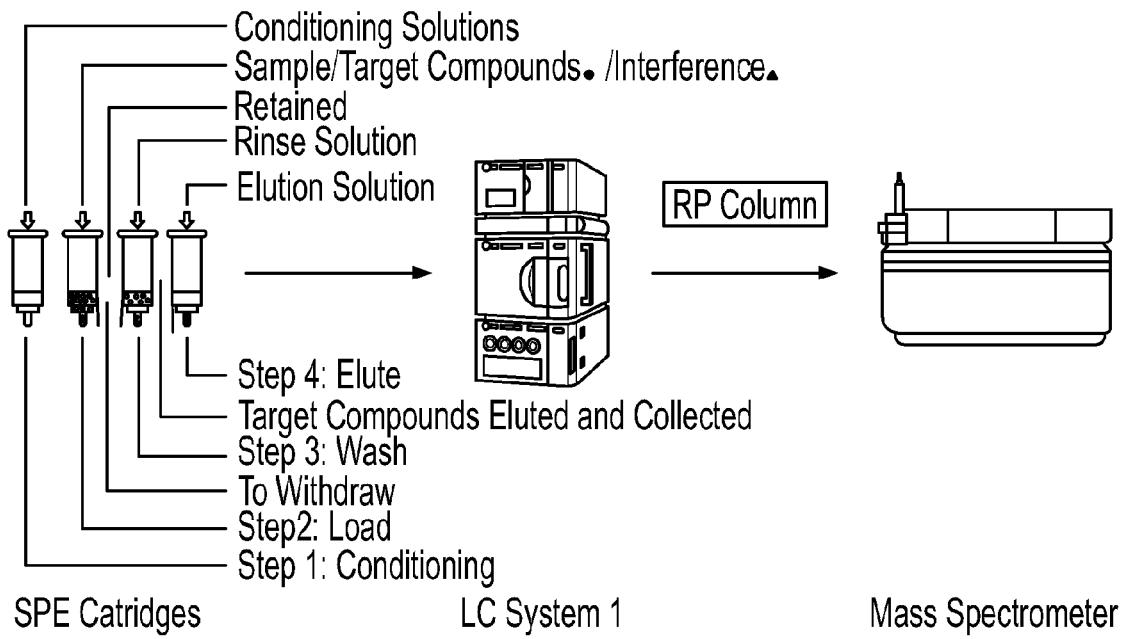
FIG. 2 is a comparison of the setups for offline 1D LC-MS/MS, traditional online 2D LC-MS/MS, and the present online continuous-flow 2D LC-MS/MS (single LC system).
Figure 2:
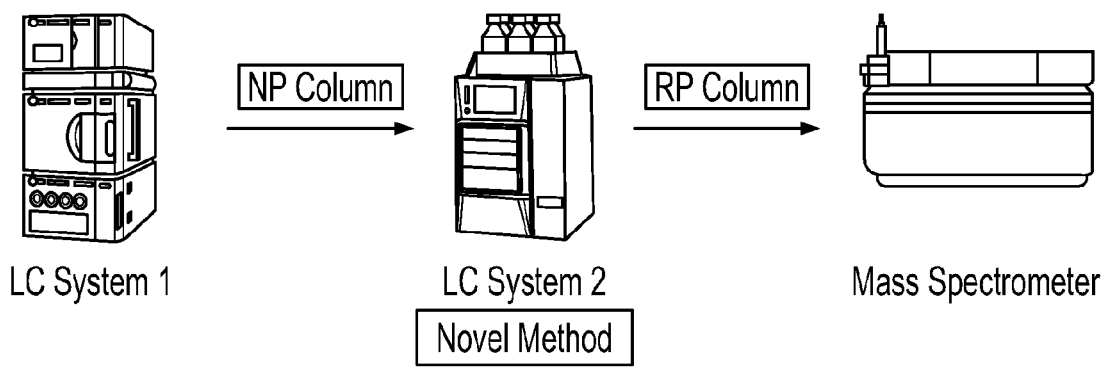
Figure 2:
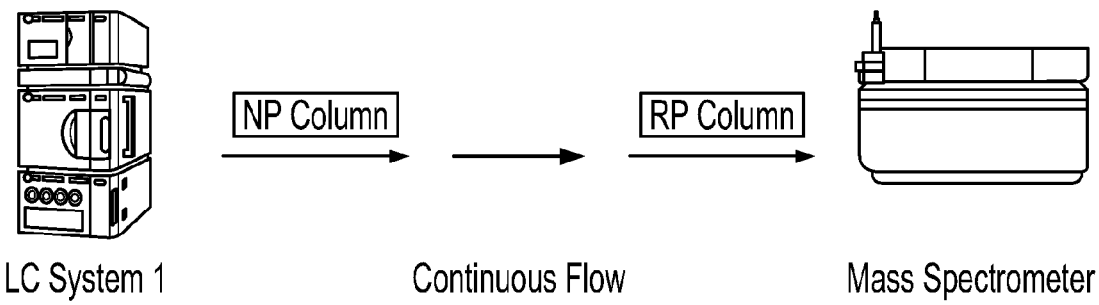

The present disclosure provides a novel method to simultaneously analyze multiple analytes in a source sample by continuous-flow two-dimensional liquid chromatography-tandem mass spectrometry (2D LC-MS/MS). In the present 2D LC-MS/MS method, a single solvent system is used as an extraction solvent as well as the mobile phase for both dimensions of the 2D LC-MS/MS analysis. During the 2D LC portion of an analytic run, a diverting valve between the two columns is switched to various positions in a timed manner so as to direct the solvent flow from the first column either to waste or to a second column for further separation. Thus, this method, while allowing for the use of two or more liquid chromatography (LC) columns, requires only one LC pump system (i.e., LC system) because the method bypasses the need for solvent exchange. In addition, the solvent flow in the present method is continuous, not interrupted by any solvent exchange step or a second LC system. By contrast, traditional 2D LC-MS/MS makes use of two separation mechanisms with two different solvent systems, e.g., one polar and one non-polar. As a consequence, two LC systems are needed.

One big advantage of the present method is the elimination of the second pump system and subsequent simplification of the 2D LC-MS/MS setup (e.g., using diverting valves with fewer ports). The elimination of the second pump system greatly reduces equipment costs and method development time. This innovation allows 2D LC-MS/MS analyses to be conducted in any lab where routine 1D LC-MS/MS analyses are currently being conducted. The innovation adds flexibility to analytical labs, allowing them to choose either 1D or 2D LC-MS/MS analyses using the same instrumentation. The simplification of the system makes personnel training faster, reduces the chances of assay failure, and reduces sample turnaround time. This method is also suitable for multiplexing, which can significantly reduce sample preparation and analysis time, as well as sampling bias, and improve reproducibility. Moreover, the novel 2D-LC approach described here can be easily adapted to work with detectors other than mass spectrometers, such as charged aerosol detectors (CAD), light-scattering detectors, or UV detectors. This flexibility greatly increases the applicability of the present analytical method.

Due to these improvements, the present analytical method will allow 2D LC-MS/MS techniques to be widely employed in the biochemical analytical field for biopharmaceutical research, medical diagnosis, and environmental studies.

Sample Preparation

The present method can be used to analyze (e.g., detect and/or quantify) one or more analytes of interest in any sample matrix, such as biological or environmental samples. A biological sample may be a sample from humans, plants, animals, or any living organelles, such as cell and tissue cultures, tissue biopsy, whole blood, dry blood spot, plasma, de-proteinated plasma, serum, de-proteinated serum, semen, sputum, urine, feces, perspiration, saliva, bile, tears, cerebrospinal fluid, swabs from body sites, skin, and hair. An environmental sample may be an air sample, soil sample, water sample, food sample, and any material sample. Analytes of interest may be, for example, small molecules such as drug substances and biomolecules such as polypeptides, peptides, nucleic acids, lipids or fatty acids, carbohydrates, hormones, vitamins, steroids, and metabolites.

To remove a majority of contaminants and interfering materials before applying the sample to the 2D LC system, analytes of interest can be enriched and isolated by filtration, precipitation, centrifugation, extraction, dilution, or a combination thereof. By way of example, analytes of interest are enriched from a source sample by solid phase extraction (SPE). SPE enriches analytes of interest by using sample preparation cartridges. The SPE extract containing the analytes may be dried and reconstituted in a solvent system compatible with the 2D LC system. If the SPE extraction solvent is compatible with the 2D LC system, as in some embodiments of the present method, there is no need for the drying and reconstitution steps.

Analytes of interest may also be extracted from a source sample by liquid-liquid extraction (LLE). LLE is used to separate analytes based on their relative solubilities in two immiscible or partially miscible liquids, usually a polar solvent like water and a non-polar organic solvent. The target analyte is first partitioned by a solvent, after which it is extracted, concentrated, and diluted.

Analytes of interest may also be extracted from a source sample by solid supported liquid-liquid extraction (SLE). In SLE, an aqueous solution of the source sample is loaded onto a support comprising of diatomaceous earth. Following sample absorption into the support, it is washed several times with an organic extraction solvent such as methyl tert-butyl ether. After the analyte of interest has been partitioned into the organic phase, it is concentrated by drying before being reconstituted in a solvent compatible for the 2D LC system such as a 50:50 methanol:water solution.

If analytes of interest are proteins, they also may be enriched from the source sample by protein precipitation extraction (PPE). Protein precipitation methods may include desalting, isoelectric point precipitation, and organic solvent extraction. By way of example, the source sample is prepared for 2D LC loading by desalting. This protein precipitation technique relies on the protein being "salted out" of the solution in response to increasing concentration of a neutral salt such as ammonium sulfate. In another example, the source sample is prepared by isoelectric point precipitation; this method may be used to precipitate contaminant proteins, rather than the target protein. The isoelectric point (pI) is the pH at which the net primary charge of a protein becomes zero. For most proteins, the pI lies in the pH range of 4-6. Inorganic acids such as hydrochloric acid and sulfuric acid may be used as precipitants. A potential disadvantage to isoelectric point precipitation is the irreversible denaturation caused by the inorganic acids.

The solvent used to extract and enrich analytes of interest from the source sample may be compatible with the 2D LC system. That is, the extraction solvent containing the extracted analyte(s) may be loaded directly to the 2D LC system without the need for a solvent exchange. In some embodiments, the extraction solvent for biomolecules (e.g., polypeptides, peptides, nucleic acids, lipids, hormones, vitamins, steroids, and carbohydrates) comprises methanol, acetonitrile, and/or water, where the ratio of these three substances can be varied depending on the analyte of interest. For example, to extract lipids from blood samples or tissue, a solvent comprises a mixture of methanol, acetonitrile, and water in a total volume percentage of 100%, e.g., about 30-100% methanol (v/v), about 0-100% acetonitrile (v/v), and about 0-50% water (v/v). The solvent may contain other ingredients as desired, e.g., 10 mM ammonium acetate and 1% formic acid. For example, the extraction solvent may contain 80% methanol, 15% acetonitrile, 5% water, 10 mM ammonium acetate, and 1% formic acid; or may contain 80% methanol, 20% acetonitrile, 10 mM ammonium acetate, and 1% formic acid. See also Chuang et al., *Methods Mol Biol*. (2016) 1378:263-72. Specific solvent compositions will depend on the target analyte and interference matrix property.

Two-Dimensional Liquid Chromatography

Once the source sample has been processed by, e.g., enriching the analytes of interest, the processed sample can be input into the liquid chromatography pump system for application to the first liquid chromatography column.

Liquid chromatography (LC) is a process of selectively retaining one or more components of a fluid solution as the fluid solution (mobile phase) permeates through a column of a finely divided substance (stationary phase) by capillary action. The retention of selective components in the fluid solution by the stationary phase results from the higher affinities of the components for the stationary phase than for the mobile phase. Liquid chromatography as used herein includes, but is not limited to, high performance liquid chromatography (HPLC), ultra-high performance liquid chromatography (UHPLC), high turbulence liquid chromatography (HTLC), normal phase chromatography (NPC), reverse phase chromatography (RPC), supercritical fluid chromatography (SFC), affinity chromatography, ion exchange chromatography (IEX), capillary liquid chromatography, electrochromatography, membrane chromatography, monolith chromatography, nano and capillary liquid chromatography, and size-exclusion chromatography (SEC). Analytes of interest may be retained by the stationary phase and subsequently eluted, or may flow through the stationary phase without being retained. Analytes in the eluate or the effluent may be monitored by a variety of means (e.g., UV, fluorescence, light scattering, or electrical conductivity) based on retention time, peak intensity, and peak area. Further detailed analysis of the analytes may be performed with techniques such as mass spectrometry as described below.

A liquid chromatography (LC) system typically comprises some or all of the following components.

(i) Injector: also known as a sample manager or auto sampler, an injector is used to introduce a source sample into a mobile phase that transfers it into an LC column.

(ii) Reservoir: a solvent reservoir holds the solvent system (mobile phase) used in the liquid chromatographic separation.

(iii) Pump: a high-pressure pump is typically used to generate and maintain a specified flow rate of the mobile phase. Traditionally, each LC column requires a dedicated pump system (iv) Column: an LC column includes an inlet port for receiving a sample and an outlet port for releasing an effluent, and is typically packed with a solid adsorbent medium such as silica, polymers, and other resins. An LC column may be, for example, a normal phase column (usually hydrophilic), a reverse phase column (usually hydrophobic), a cation exchange column, an anion exchange column, a size exclusion chromatography column, membrane column, monolith column, nano or capillary LC column, and a chiral chromatography column.

(v) Valves: diverter or switching valves are high-pressure valves between a column and the next destination of the eluate or effluent coming through the column. The next destination can be, for example, a waste collector, or an analyte detector. A diverter (or divert) valve can be controlled manually or by a computer, and can optionally include a trap column. Typically, a diverter valve used in an LC system can have as many as 12 ports.

(vi) Accessories: high-pressure tubes and fittings are used to interconnect the sample injector, solvent reservoir, pump, column, and detector to form a conduit for the mobile phase.

A 2D LC system has two LC columns with two orthogonal separation mechanisms. The first LC column is referred to as the first dimension ($^1$D), and the second LC is referred to as the second dimension ($^2$D). A sample containing one or more target analytes is injected into the first LC column with a compatible solvent. The solvent flows through the column at high pressure, wherein the target analytes are separated from the contaminants in the sample. The effluent from the first LC column is collected and injected into the second LC column, where the target analytes are further resolved. Alternatively, the $^1$D eluate can be retained in a trap column before being injected into the second dimension. Guard columns containing a stationary phase similar to that of the $^2$D column may be used as trap columns. After elution from the second dimension, the effluent containing the target analytes can be further analyzed.

There are generally two types of 2D LC. In comprehensive 2D LC (LC×LC), the whole stream of the $^1$D effluent is directed to the $^2$D column. In heart-cutting 2D LC (LC–LC), a specific effluent peak or a specific part of the chromatogram is directed to the $^2$D column. Multiple peaks or multiple parts of the chromatogram can also be selected for transfer to the $^2$D column. Diverting valves in the LC system allow for cutting and storage of multiple cuts, which are then analyzed in the $^2$D column.

FIG. 1 illustrates a typical heart-cutting 2D LC system, in which solid lines indicate the flow direction of the mobile phase. In step 1, the first LC system, with a normal phase (NP) column, separates lipid analytes of interest from interfering phospholipids. A 10-port diverting valve directs effluent containing the analytes to a trap column, where the analytes are retained by the trap column, while the phospholipids exit the trap column and continue onto a waste collector. In step 2, a second LC pump system inputs a fluid compatible with the second LC column (reverse phase or RP); this fluid, through control of the position of the 10-port valve, flows through the trap column, achieving solvent exchange in the trap column. In step 3, the second LC pump inputs the second mobile phase solvent, which runs through the trap column, and through positioning of the diverting valve, brings the analytes to the RP column. The analytes are further separated by the RP column and eventually are analyzed by a mass spectrometry.

In the novel 2D LC systems of the present disclosure, only one LC pump system is needed. The flow from the first column to the second column can be continuous, without the need for the step of solvent exchange. This is possible because one mobile phase solvent system is used. While the composition of the mobile phase solvent system (e.g., the relative ratio of the ingredients) can be adjusted in a timed fashion as the analytes travel through the separation system, there is no need for solvent exchange as the analytes move from one column to the next because the solvent system, even with adjustment of its ingredients, is compatible with both columns. A diverting valve between the two columns can direct the effluent from the first column to waste or to the second column, depending on the analyte's expected time of exit from the first column. Because there is no more need for solvent exchange, the diverting valve between the two columns can be simpler, requiring fewer ports. The novel 2D LC systems of the present disclosure encompass both comprehensive 2D LC and heart-cutting 2D LC systems.

Figure 3:
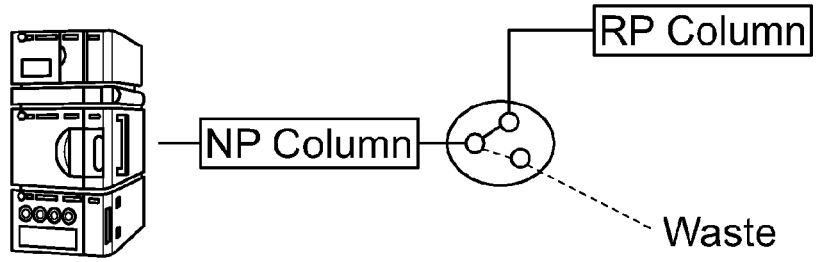
FIG. 3 is a schematic representation illustrating the present continuous-flow 2D LC-MS/MS methodology.
Figure 3:
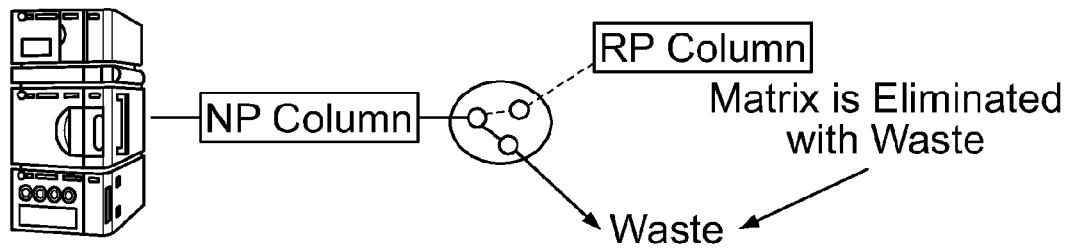
Figure 3:
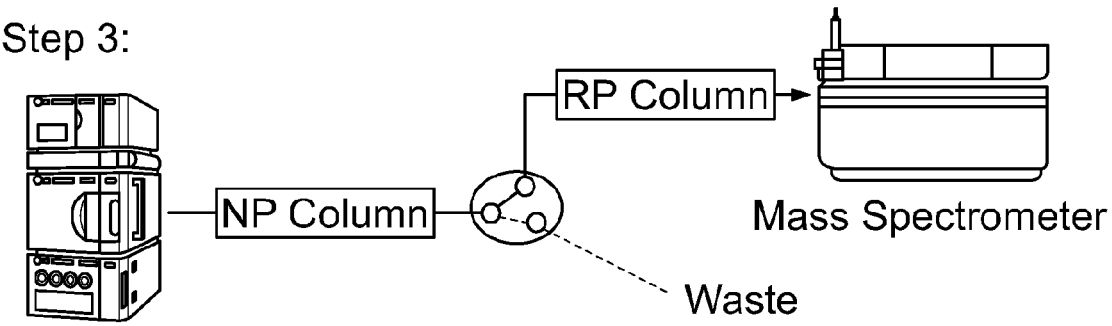

FIG. 3 illustrates a heart-cutting embodiment of the novel 2D LC systems of the present disclosure. In step 1, the LC system inputs the sample with a solvent system having a first mobile phase ratio to a NP column, where this solvent system, through the position of a three-port diverting valve, brings certain analytes of interest to a RP column, where they are retained. In step 2 (i.e., a later time point), the diverting valve is switched to a second position, such that the NP column effluent carrying interfering matrix is directed to waste. In step 3, additional analytes from the NP column travel to the RP column, and all the target analytes retained by the RP column are eluted by the solvent system with a different mobile phase ratio input by the LC pump system. The target analytes eluted from the RP column are then subject to further analysis such as mass spectrometry analysis. Since the solvent system for the entire LC run contains the same compatible components (though at varied ratios as the run progresses), there is no need to interrupt the solvent flow to perform a solvent exchange. Furthermore, only one pump system (shown as "LC System 1") is needed, in contrast to the traditional 2D LC system.

The $^1$D and $^2$D columns in the present novel systems may be selected based on the nature of target analytes and matrix interference components. In some embodiments, the $^1$D column is a normal phase column and the $^2$D column is a reverse phase column, as illustrated above. In some embodiments (e.g., for carbohydrate analytes), the $^1$D column is a normal phase column and the $^2$D column is a weak anion exchange column. In some embodiments (e.g., for protein/peptide analytes), the $^1$D column is a normal phase column and the $^2$D column is a reverse phase column. In some embodiments (e.g., for oligonucleotide analytes such as circulating tumor cell (CTC) DNA), the $^1$D column is a normal phase column and the $^2$D column is a reverse phase column with an ion-pairing reagent.

The LC solvents may include, without limitation, water, methanol, ethanol, acetonitrile, trifluoroacetic acid, heptafluorobutyric acid, ether, hexane, ethyl acetate, and an organic solvent such as hydrocarbon solvents (e.g., aliphatic and aromatic solvents), oxygenated solvents (e.g., alcohols, ketones, aldehydes, glycol ethers, esters, and glycol ether esters), and halogenated solvents (e.g., chlorinated and brominated hydrocarbons). The LC solvents may be buffered and may contain ammonium acetate, ammonium formate, ammonium bicarbonate, acetic acid, trifluoroacetic acid, formic acid, trimethylamine, and triethylamine. In some embodiments, the solvent system used for the present 2D LC systems is compatible with the extraction solvent and may contain methanol, acetonitrile, and water. In certain embodiments, the solvent system contains about 0-100% methanol, about 0-100% acetonitrile, and about 0-90% water, with a total volume percentage of 100%. In particular embodiments, the solvent system for the 2D LC system is a mixture of mobile phase A (mobile phase solvent A) and mobile phase B (mobile phase solvent B) at various ratios, where mobile phase A contains water and 0.5% trifluoroacetic acid, and mobile phase B contains 85% methanol, 15% acetonitrile, and 0.5% trifluoroacetic acid.

By way of example, a source sample comprising one or more lipid analytes (e.g., sphingolipids, cholesterol, and triglycerides) is extracted with an extraction solvent comprising 80% methanol, 15-20% acetonitrile, and 0-5% water (e.g., 80% methanol, 15% acetonitrile, and 5% water; or 80% methanol and 20% acetonitrile). The extraction solvent may optionally contain 10 mM ammonium acetate and 1% formic acid. The extracted sample is then loaded to an LC system using a mobile phase solvent system comprising acetonitrile, methanol, and water, wherein the lipid analytes are separated from major matrix contaminants (carbohydrates, proteins, nucleotides, etc.). The solvent system may further comprise 10 mM ammonium acetate, 1% formic acid, and 0.5% trifluoroacetic acid. The first LC column is a NP column, wherein less polar lipids are eluted first and are directed to a reverse phase column through a diverting valve, while more polar lipids are retained in the NP column. Next, the diverting valve is switched to the waste position for elimination of NP column effluent carrying the matrix contaminants. The diverting valve is then switched back to the original position to transfer the still more polar lipid analytes, previously retained in the NP column, into the second dimension for further resolution. The timing of valve switching is adjusted to regulate solvent flow to either waste or to the second column. In the RP column, more polar lipid analytes are eluted first, while less polar lipid analytes are retained in the column until more hydrophobic eluting solvent is used. The resolved lipid analytes can then be further analyzed, for example, by mass spectrometry.

Also by way of example, a sample comprising one or more protein/peptide analytes, e.g., insulin, is extracted with an extraction solvent comprising methanol, acetonitrile and water. The extraction solvent may further comprise 0.5% acetic acid and 0.01% trifluoroacetic acid. The extracted sample is then injected into the first column, e.g., a normal phase column, using a mobile phase solvent system comprising acetonitrile, methanol and water, wherein the protein/peptide analytes are separated from major matrix contaminants (carbohydrates, lipids, nucleotides, etc.). The solvent system may further comprise 0.5% acetic acid and 0.01% trifluoroacetic acid. In some embodiments, the first dimension is a normal phase column, wherein more hydrophobic phospholipids are eluted first, while more hydrophilic polypeptides are retained in the normal phase column. In some other embodiments, the first dimension is an anion exchange column, wherein positively charged polypeptides are eluted first and transferred to the second dimension through the diverting valve, while negatively charged polypeptides are retained in the anion exchange column. Next, the diverting valve is switched to waste to eliminate matrix contaminants. The diverting valve is switched back to the original position to transfer the polypeptides, previously retained in the first dimension, into the second dimension for further resolution. The timing of valve switching to regulate solvent flow to either waste or to the second column, and solvent gradient design, can be easily adjusted to separate different protein analytes, as well as to eliminate matrix interference. In further embodiments, the second dimension is a reverse phase column, wherein polar proteins are eluted first, while nonpolar proteins are retained in the column until more hydrophobic eluting solvent is used. The resolved protein analytes can then be further analyzed, for example, by mass spectrometry.

Also by way of example, a sample comprising one or more nucleic acid analytes, e.g., synthetic oligonucleotides, is extracted with an extraction solvent comprising water and acetonitrile. The extracted sample is then injected into a silica column, e.g., a normal phase column, using a mobile phase solvent system comprising methanol, acetonitrile, and water, wherein the nucleic acid analytes are separated from major matrix contaminants (carbohydrates, lipids, proteins, etc.). The solvent system may further comprise trimethylamine or triethylammonium bicarbonate. Next, the diverting valve is switched to waste to eliminate matrix contaminants. The diverting valve is switched back to the original position to transfer the nucleic acid analytes, previously retained in the first dimension, into the second dimension for further resolution. The timing of valve switching to regulate solvent flow to either waste or to the second column, and solvent gradient design, can be easily adjusted to separate different nucleic acid analytes, as well as to eliminate matrix interference. In further embodiments, the second dimension is a C18 column using ion-pairing mechanism, e.g., a reverse phase column. The resolved nucleic acid analytes can then be further analyzed, for example, by mass spectrometry.

Also by way of example, a sample comprising one or more carbohydrate analytes, e.g., N-linked Fetuin oligosaccharides, is extracted with an extraction solvent comprising methanol, acetonitrile, and water. The extraction solvent may further comprise 10 mM ammonium acetate, 0.5% acetic acid, and 0.1% formic acid. The extracted sample is then injected into a silica column, e.g., a normal phase column, using a mobile phase solvent system comprising methanol, acetonitrile, and water, wherein the carbohydrate analytes are separated from major matrix contaminants (lipids, proteins, nucleic acids etc.). The solvent system may further comprise 10 mM ammonium acetate, 1% formic acid, and 0.5% trifluoroacetic acid. Next, the diverting valve is switched to waste to eliminate matrix contaminants. The diverting valve is switched back to the original position to transfer the carbohydrate analytes, previously retained in the first dimension, into the second dimension for further resolution. The timing of valve switching to regulate solvent flow to either waste or to the second column, and solvent gradient design, can be easily adjusted to separate different carbohydrate analytes, as well as to eliminate matrix interference. In further embodiments, the second dimension is a weak-anion exchange column. The resolved carbohydrate analytes can then be further analyzed, for example, by mass spectrometry.

Also by way of example, a sample comprising one or more steroid analytes, e.g., dihydrotestosterone, is extracted with an extraction solvent comprising methanol, acetonitrile, and water. The extraction solvent may further comprise 10 mM ammonium acetate, 0.5% acetic acid, and 1% formic acid. The extracted sample is then injected into a silica column, e.g., a normal phase column, using a mobile phase solvent system comprising methanol, acetonitrile, and water, wherein the steroid analytes are separated from major matrix contaminants (carbohydrates, lipids, proteins, nucleic acids etc.). The solvent system may further comprise 10 mM ammonium acetate, 0.5% acetic acid, and 0.5% trifluoroacetic acid. Next, the diverting valve is switched to waste to eliminate matrix contaminants. The diverting valve is switched back to the original position to transfer the steroid analytes, previously retained in the first dimension, into the second dimension for further resolution. The timing of valve switching to regulate solvent flow to either waste or to the second column, and solvent gradient design, can be easily adjusted to separate different steroid analytes, as well as to eliminate matrix interference. In further embodiments, the second dimension is a C18 column, e.g., a reverse phase column. The resolved steroid analytes can then be further analyzed, for example, by mass spectrometry.

Mass Spectrometry

The analytes separated by the present novel 2D LC system can be further analyzed by a technique of choice. In many cases, mass spectrometry (MS) is used due to its ultra-high sensitivity. A mass spectrometer ionizes the target analytes, separates the resulting ions in vacuum based on their mass-to-charge ratios, and ultimately measures the intensity of each ion. MS is extremely useful for qualitative and quantitative analysis because the mass spectra can indicate the concentration levels of ions that have a given mass.

A mass spectrometer consists of three main components: an ion source for analyte ionization, a mass analyzer that separates the ions based on their mass-to-charge (m/z) ratio, and a detector that detects the separated ions. In the ionizer, the $^2$D effluent is nebulized, desolvated, and ionized, generating charged particles—ions. The ions migrate under vacuum through a series of mass analyzers. Precursor ions with specific (m/z) ratios are selected to pass through the mass analyzer, excluding all other (m/z) ratio particles. The separated ions are then detected, for example, by an electron multiplier. Ionization of the sample may be performed by, for example, electrospray ionization (ESI), atmospheric pressure chemical ionization (ACPI), photoionization, electron impact ionization, chemical ionization, fast atom bombardment (FAB)/liquid secondary ion mass spectrometry (LSIMS), matrix assisted laser desorption ionization (MALDI), field ionization, field desorption, thermospray/plasmaspray ionization, or particle beam ionization. The ions may be detected by, for example, multiple reaction monitoring (MRM), selective ion monitoring mode (SIM)), selected reaction monitoring (SRM), or electron multiplier.

MS data is relayed to a computer, which plots voltage versus time. Concentrations of one or more target analytes in the source sample may be determined by comparing the area under the peaks in the chromatogram to a calibration curve or by comparing the ratio of internal standards to test samples.

In some embodiments of the present disclosure, the mass spectrometric method utilizes "tandem mass spectrometry" or "MS/MS," wherein the selected precursor ions are further fragmented into product ions, for example, by collision with an inert gas such as argon, helium or nitrogen. A second mass analyzer is used to target specific product ion fragments for detection. The selection-fragmentation-detection sequence can be further extended to the first-generation product ions. For example, selected product ions can be further fragmented to produce another group of product ions and so on. The fragmentation pattern of ions is highly specific to the structure of a compound and therefore allows for precise structure determination.

In some embodiments, the mass analyzer may be selected from a quadrupole analyzer, an ion trap analyzer, a Fourier transform ion cyclotron resonance (FTICR) mass analyzer, an electrostatic trap analyzer, a magnetic sector analyzer, quadrupole ion trap analyzer, and a time-of-flight analyzer (both MALDI and SELDI).

A 2D LC-MS system of the present disclosure further comprises an interface that relays the purified target analytes from the $^2$D column into the mass spectrometer. This interface is used because of the inherent incompatibility of liquid chromatography and mass spectrometry. While the mobile phase solvent system in an LC system is a pressurized fluid, the MS device commonly operates under vacuum. The interface transfers the target analytes from the LC unit to the MS unit, removes a significant portion of the mobile phase solvent system used in the liquid chromatographic separation process, and preserves the chemical identity of the target analytes.

In some embodiments, the interface is electrospray interface. Alternatively, the interface may be an atmospheric pressure ionization interface, atmospheric pressure chemical ionization interface, thermospray interface, moving-belt interface, direct liquid introduction interface, particle beam interface, or a fast atom bombardment (FAB) based interface.

2D LC-MS combines the exceptional separation power of liquid chromatography with the exceptional sensitivity and selective mass analysis capabilities of mass spectrometry to provide molecular mass and structural information for components in a mixture. This information may be supplemented with information derived from other LC detectors including, but not limited to, refractive index detectors, chiral detectors, radio flow detectors, UV detectors, fluorescence detectors, light scattering detectors, and electrical conductivity detectors.

Applications

The novel 2D LC-MS systems, including the novel 2D LC-MS/MS systems, of the present disclosure can be used to analyze (including detecting and quantifying) a variety of molecules, including small molecules (e.g., drug substances) and large molecules (e.g., biomolecules).

In some embodiments, the present 2D LC-MS/MS systems are used to monitor biomarkers in pre-clinical and clinical research and development for screening/diagnostic and therapeutic purposes. By way of example, a 2D LC-MS/MS system may be used to measure the levels of certain lipid biomarkers in lysosomal storage disorders such as Fabry Disease, Gaucher Disease, Krabbe Disease, and acid sphingomyelinase deficiency (ASMD; e.g., Niemann-Pick Disease (NPD) type A, type B, and type A/B).

As further illustrated in the Working Examples below, a 2D LC-MS/MS system can be used to analyze two lipid biomarkers in blood samples from ASMD patients: ceramide (CER) and lyso-sphingomyelin (lyso-SPM). ASMD is a disorder of sphingolipid metabolism resulting in the accumulation of sphingomyelin in tissues throughout the body, in particular the spleen, liver, lungs, bone marrow, and in some cases brain. Elevated levels of lyso-SPM (sphingosine phosphocholine) are common as well. The deficient enzyme in the patients, acid sphingomyelinase, catalyzes the hydrolytic cleavage of sphingomyelin in lysosomes, producing phosphocholine and ceramide. Since lipids such as ceramide and lyso-SPM are highly elevated in ASMD patients, they can be used as biomarkers to screen and diagnose ASMD as well as to monitor enzyme replace therapy (with recombinant human ASM such as olipudase alfa).

In order that this invention may be better understood, the following examples are set forth. These examples are for purposes of illustration only and are not to be construed as limiting the scope of the invention in any manner.

EXAMPLES

Example 1: 2D LC-MS/MS Detection of Ceramide and Lyso-SPM in Human Plasma

This Example describes the use of a novel 2D LC-MS/MS system of the present disclosure to analyze ceramide (CER) and lyso-SPM in human plasma samples.

Chemicals & Reagents

Standard reference ceramide (from porcine brain) was purchased from Avanti Polar Lipids (AL, USA). CER internal standard (N-Nonadecanoyl-D-erythro-sphingosine) and lyso-sphingomyelin standard (sphingosylphosphorylcholine) were purchased from Matreya (PA, USA). Lyso-SPM internal standard (d9-lysosphingomyelin) was synthesized in house. Methanol and acetonitrile (both HPLC grade) were purchased from Honeywell (NC, USA). Ammonium acetate was purchased from Sigma Aldrich (MO, USA). Deionized water was obtained using an in-house MilliQ DI system (Millipore, MA, USA). Formic acid (Optima™ LC/MS grade) was purchased from Fisher Scientific (Hampton, NH). Trifluoroacetic acid (TFA) was purchased from EMD Millipore (MA, USA).

Lipid Extraction

10 μL of human plasma were mixed with 800 μL of assay working solution (80% methanol, 20% acetonitrile, 10 mM ammonium acetate, and 1% formic acid) containing internal standards (IS) for CER (0.22 μg/mL) in a 96-well plate. Following vortexing for 10 min at 11,000 rpm on a DVX-2500 multi-tube vortexer (VWR Scientific Products, NJ, USA) and sonicating for 10 min in a water bath (Branson 3510 Ultrasonic Cleaner, Marshall Scientific, NH, USA), the plates were subjected to 5 min centrifugation in a counter centrifuge (Beckman Coulter, CA, USA). The supernatant was transferred to a new 96-well plate and submitted to 2D LC-MS/MS analysis. The CER concentration in each sample was quantified as μg/mL and lyso-SPM was quantified as ng/mL in plasma based on a standard curve using a linear fit.

LC-MS/MS System Setup

2D LC-MS/MS analyses were conducted using an Acquity UPLC System (Waters Corp., Milford, MA, USA)

and an API 4000 Quadrupole Mass Spectrometer (AB Sciex, Toronto, Canada). The 2D LC-MS/MS system was controlled by the Analyst® software (AB Sciex). Data processing and analysis was conducted using Microsoft Excel and Watson LIMS™ Software (Thermo Fisher Scientific, Waltham, MA).

The setup for 2D LC consisted of a silica column (Ultra Silica column, 2.1×150 mm, 5.0 µm, Restek, PA, USA) for the first dimension, and a C18 column (Acquity UPLC BEH C18 column, 2.1×100 mm, 1.7 µm, Waters Corp.) for the second dimension. Both HPLC columns were placed inside the Acquity Column Manager such that each column occupied a different compartment within the Column Manager, and both columns were kept at the same temperature (60° C.). The setup for 2D HPLC comprised the following connections:

a) a PEEK tube (approximately 60 cm in length) connecting the outlet of the first dimension analytical column to port 1 of the diverting valve;
b) a second PEEK tube (approximately 70 cm in length) connecting port 2 of the diverting valve to the inlet of the second dimension analytical column;
c) a third PEEK tube (approximately 80 cm in length) connecting the outlet of the second dimension analytical column to the mass spectrometer; and
d) a fourth PEEK tube (at least 60 cm in length) connecting port 3 of the diverting valve to waste.

Mobile Phases

Mobile phase A was water plus 0.5% trifluoroacetic acid. Mobile phase B was 85% methanol, 15% acetonitrile, and 0.5% trifluoroacetic acid. Mobile phase A and mobile phase B were mixed at different ratios and loaded to the LC system at pre-determined time points of the run as indicated in Table 1 below. The injection volumes were 2 µL injections for the sample, and the mobile phase flow speed was 0.2 mL/min.

TABLE 1

2D LC Solvent Conditions

| Time Point (min) | % A | % B |
| --- | --- | --- |
| 0.0 | 15 | 85 |
| 2.00 | 15 | 85 |
| 2.20 | 30 | 70 |
| 4.00 | 30 | 70 |
| 4.20 | 1 | 99 |
| 17.50 | 1 | 99 |
| 17.60 | 15 | 85 |
| 20.00 | 15 | 85 |

LC Diverting Valve Conditions

In coordination with the adjustment of the solvent system as indicated in the table above, the diverting valve of the 2D LC system was switched to different port positions at predetermined time points as indicated in Table 2 below, to allow different fractions of the $^1$D effluent to be directed to either waste or to the next (RP) column. See also FIG. 4.

TABLE 2

2D LC-MS/MS Divert Valve Conditions

| Time Point (min) | Valve Position | Ceramide | Phospholipids | Lyso-Sphingomyelin |
| --- | --- | --- | --- | --- |
| 0.0-0.3 | A (waste) | NP Column (elution) | NP Column (elution) | NP Column (elution) |
| 0.3-2.5 | B (RP column) | RP Column (retained) | NP Column (elution) | NP Column (elution) |
| 2.5-3.6 | A (waste) | RP Column (retained) | Majority to Waste (elution) | NP Column (elution) |
| 3.6-19.0 | B (RP column) | Elution from RP to mass spec (10.0-18.0 min) | Elution from RP to mass spec (trace amounts only) | Elution from RP to mass spec (5 min) |
| 19.0-20.0 | A (waste) Re-equilibration | N/A | N/A | N/A |

Mass Spectrometry Analysis

The multiple reaction monitoring (MRM) technique was used to analyze the ceramide and lyso-SPM. This technique uses a triple quadrupole MS that first targets the ion corresponding to the compounds of interest—ceramide and lyso-SPM—with subsequent fragmentation of that target ion to produce a range of daughter ions. One (or more) of these fragment daughter ions are selected for quantitation purposes. Only compounds that meet both these criteria, i.e., specific parent ion and specific daughter ions corresponding to the mass of the compounds are isolated within the mass spectrometer.

The MRM channel parameters in the API 4000 Mass Spectrometer are shown in Table 3 below.

TABLE 3

Ceramide MRM Channels

| | Q1 Mass (Da) | Q3 Mass (Da) | Dwell (msec) | ID | DP (volts) | EP (volts) | CE (volts) | CXP (volts) |
| --- | --- | --- | --- | --- | --- | --- | --- | --- |
| 1 | 538.500 | 264.300 | 50.0 | C16:0 | 60.0 | 10.0 | 37.0 | 10.0 |
| 2 | 548.700 | 264.400 | 50.0 | C18:0-H2O | 155.0 | 10.0 | 37.0 | 10.0 |
| 3 | 566.700 | 264.400 | 50.0 | C18:0 | 60.0 | 10.0 | 37.0 | 10.0 |
| 4 | 594.800 | 264.400 | 50.0 | C20:0 | 60.0 | 10.0 | 37.0 | 10.0 |
| 5 | 594.800 | 292.300 | 50.0 | C20:0 | 60.0 | 10.0 | 37.0 | 10.0 |
| 6 | 620.000 | 264.500 | 50.0 | C22:1 | 60.0 | 10.0 | 37.0 | 10.0 |
| 7 | 622.800 | 264.400 | 50.0 | C22:0 | 60.0 | 10.0 | 37.0 | 10.0 |
| 8 | 630.900 | 264.400 | 50.0 | C24:1-H2O | 155.0 | 10.0 | 37.0 | 10.0 |
| 9 | 648.800 | 264.400 | 50.0 | C24:1 | 60.0 | 10.0 | 37.0 | 10.0 |
| 10 | 650.800 | 264.400 | 50.0 | C24:0 | 60.0 | 10.0 | 37.0 | 10.0 |
| 11 | 676.800 | 264.500 | 50.0 | C26:1 | 60.0 | 10.0 | 37.0 | 10.0 |

Table 4 shows the MRM channel parameters for ceramide internal standard (IS), lyso-SPM analyte, and lyso-SPM IS.

TABLE 4

Ceramide IS, Lyso-SPM, and Lyso-SPM IS MRM Channels

| | Q1 Mass (Da) | Q3 Mass (Da) | Time (sec) | ID | DP (volts) | EP (volts) | CE (volts) | CXP (volts) |
|---|---|---|---|---|---|---|---|---|
| 1 | 465.100 | 183.900 | 50.0 | Lyso-SPM | 85.0 | 10.5 | 32.0 | 16.0 |
| 2 | 474.400 | 193.300 | 50.0 | D9-Lyso-SPM | 10.5 | 10.5 | 32.0 | 16.0 |
| 3 | 580.800 | 264.400 | 50.0 | CER-IS | 10.0 | 10.0 | 35.0 | 10.0 |
| 4 | 562.800 | 264.400 | 50.0 | CER-IS - $H_2O$ | 10.0 | 10.0 | 35.0 | 10.0 |

Results

In this novel analytic method, CER and lyso-SPM were simultaneously extracted with an assay working solution that was compatible with the mobile phase solvent system used later in the 2D LC system. The extraction sample was then directly injected into the first column and transferred into the second column by continuous flow without the need for solvent exchange. We found that normal phase chromatography was well-suited for the separation of CER and lyso-SPM from phospholipids. Thus, this approach was used as the first dimension of separation by LC. A second dimension of separation using reverse phase chromatography was used to separate CER and lyso-SPM from structurally related compounds such as glycosphingolipids and lyso-glycosphingolipids.

More specifically, in this LC process, the diverting valve was set at position A at the outset, to allow flushing of the columns. The valve was then set at position B, and ceramide, which was separated from phospholipids in the normal phase (NP) column, flowed to the RP column and was retained in the RP column. The diverting valve was then switched to waste (position A) to eliminate phospholipids and other matrix components that followed in the $^1$D effluent. Finally, the diverting valve was switched to position B again to allow lyso-SPM to enter the RP column, where both the ceramide and lyso-SPM were separated from other potential interfering molecules prior to mass spectrometry analysis.

Figure 4:
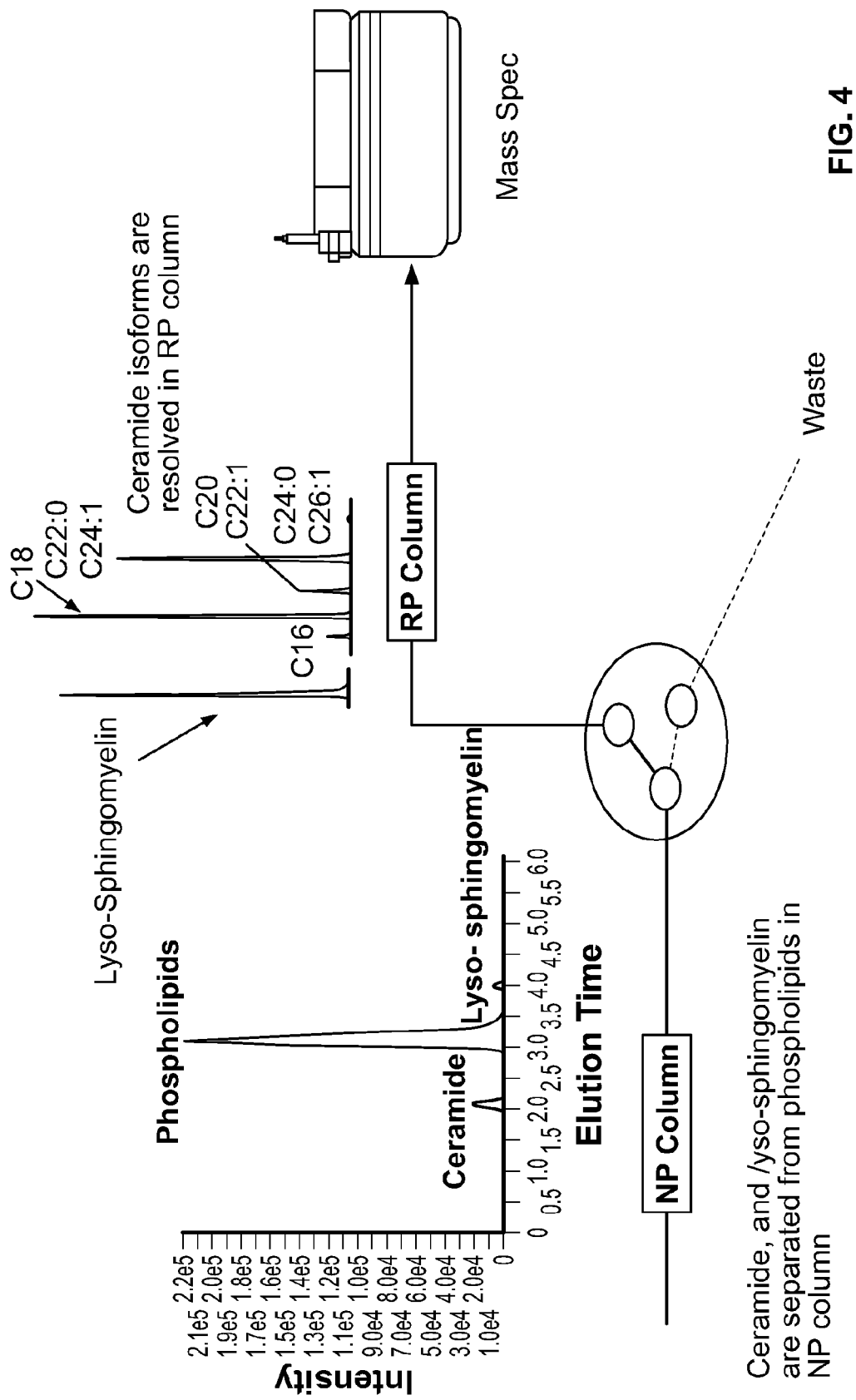
FIG. 4 illustrates the analysis of ceramide and lyso-sphingomyelin (lyso-SPM) using the present continuous-flow 2D LC-MS/MS methodology. Ceramide and lyso-SPM were separated from contaminating phospholipids in this methodology.

The data show that both CER and Lyso-SPM were successfully extracted and quantitated. As shown in FIG. 4, ceramide eluted first from the NP column, followed by the major contaminant phospholipids, and then lyso-SPM. Phospholipids were directed to waste by setting the diverting valve to position A, where the ceramide and lyso-SPM analytes were directed to the RP column by setting the valve at position B. In the RP column, the lyso-SPM appeared as a single peak, whereas the ceramide analytes were fractioned according to fatty acid chain length and number of double bonds, into distinct retention windows containing the following isoforms: C16, C18, C20 and C22:1, C22 and C24:1, C24, and C26:1. The data show that the CER isoforms eluted from the RP column as sharp peaks with little background noise, and a single peak was identified for each isoform. Several runs were performed, and they gave consistent retention times.

The above 2D LC-MS/MS methodology reduced the sample turnaround time for the CER and lyso-SPM quantitation in human plasma from the typical 8 days to only 2 days. Additionally, the original labor-intensive offline extraction work including SPE and protein precipitation (PPT) procedure for sample clean up was reduced from 25 hours to 1 hour with the utilization of the present extraction solvent and continuous flow 2D LC. See, e.g., Chuang et al., *Methods in Molecular Biology*, Vol. 1378, DOI 10.1007/978-1-4939-3182-8_28. As can be seen above, the entire 2D LC run was completed in 20 minutes.

TABLE 5

Comparison between 1D LC-MS/MS and Novel 2D-LC-MS/MS

| Method | Patient samples per extraction | Extraction time/batch | LC-MS/MS Run time/ Data process | Turnaround time for 80 samples |
|---|---|---|---|---|
| Original SPE and PPT Methods for Ceramides and lyso-SPM | 80 (4 plates needed) | 25 hours (8 hours/day) | 36 hours | 8 Days |
| Novel 2D LC-MS/MS For Ceramide and lyso-SPM | 80 (1 plate needed) | 1 hour | 32 hours | 2 Days |

Example 2: Assay Qualification of 2D LC-MS/MS Detection of Ceramide in Human Plasma This Example describes a study that qualified the 2D LC-MS/MS system for detection of ceramides. In this study, the samples, calibration curve standards, and controls were added to a 96-well plate. Then an assay working solution containing known amounts of internal standards (CER-IS) was added to the wells. The plate was then vortexed, sonicated and centrifuged as described in Example 1. After centrifugation, supernatants were transferred to a new 96-well plate. The new plate was then transferred to the 2D LC-MS/MS system for analysis as also described in Example 1.

Following sample run, the peaks corresponding to individual CER isoforms were integrated using the Analyst™ Software. The peak areas for individual CER isoforms of any given sample were then summed in Excel. The total CER peak area was imported to Watson®, which calculated the total CER concentration (μg/mL) based on total CER peak area ratio to the CER-IS peak area using the calibration curve intercept and slope.

The novel multiplex assay was qualified for CER quantitation. The qualification parameters included system suitability, within-runs and between-runs precision and accuracy, calibration (standard) curve linearity, analytical sensitivity, carryover, delipidized plasma matrix effect, reinjection reproducibility, batch size evaluation, recovery of extraction, sample dilution integrity, determination of CER reference in healthy donors, and comparison of methods to determine plasma CER levels.

Carryover was evaluated by injecting solvent (assay working solution only) after the highest calibration standard in each run. Delipidized plasma matrix effect was evaluated using three independent lots of delipidized plasma spiked with analytes at three different concentrations (low quality control or LQC, middle quality control or MQC, and high quality control or HQC). Reinjection reproducibility was evaluated by continued re-injection of samples at LLOQ (lower limit of quantification), LQC, MQC, HQC, and ULOQ (upper limit of quantification) concentrations. Recovery of extraction was assessed by comparing pre- and post-spiking of 2 pooled patient samples with CER. Internal standard (IS) was introduced in the same stage for pre- and post-spiked conditions.

The data show that the present novel 2D LC-MS/MS methodology detected 11 different CER isoforms by multiple-reaction monitoring (MRM) using independent MS/MS channels for each of these isoforms. System suitability test showed % CV between 0% and 5% in all passing runs performed throughout the validation process. The mean % Bias and mean % CV (coefficient variation) for all concentrations passed the established criteria for precision and accuracy. The analytical sensitivity was defined as the lowest concentration of an analyte that could be measured with acceptable accuracy and precision. The % CV and mean % Bias for the LLOQ were 8% and −8%, respectively.

The minimal and maximal carryover for analyte peak area was 2% and 11%, respectively. The overall % CV for delipidized plasma matrix effect measured at the three concentrations was 6% (LQC), 2% (MQC) and 3% (HQC). The % CV for reinjection reproducibility ranged from 2% to 4% for the specified concentrations. Recovery of extraction ranged from 67% to 88%, with % CV varying from 2% to 11%. The results demonstrate that the method is precise and accurate and qualified for use in measuring Ceramide concentration in human plasma.

The invention claimed is:

1. A method for analyzing one or more analytes in a source sample, comprising the steps of:
   (a) extracting the one or more analytes from the source sample with an extraction solvent to obtain an extraction sample;
   (b) applying the extraction sample and a solvent system to a first liquid chromatography (LC) column with an LC pump system, wherein the first LC column is directly connected to a second LC column through a tube with a diverting valve;
   (c) setting the diverting valve to a first position at a first predetermined time such that the solvent effluent from the first LC column is directed to waste;
   (d) setting the diverting valve to a second position at a second predetermined time such that the solvent effluent from the first LC column enters the second LC column for further separation;
   (e) repeating steps (c) and (d) as needed; and
   (f) analyzing the chromatographically separated sample obtained from the second LC column,
   wherein the method utilizes only one LC pump system for both LC columns, and
   wherein the extraction solvent is compatible with the solvent system.

2. The method of claim 1, wherein step (f) comprises using mass spectrometry (MS) to analyze the chromatographically separated sample obtained from the second LC column.

3. The method of claim 2, wherein the MS is tandem MS.

4. The method of claim 1, wherein the LC is high performance liquid chromatography or ultra-high performance liquid chromatography.

5. The method of claim 1, wherein the first LC column is a normal phase column and the second LC column is a reverse phase column, or vice versa.

6. The method of claim 1, wherein the solvent system comprises one or more of methanol, acetonitrile, and water.

7. The method of claim 6, wherein the solvent system further comprises ammonium acetate and/or formic acid.

8. The method of claim 1, wherein the relative ratios of the components of the solvent system are varied during a single sample run.

9. The method of claim 1, wherein the source sample is a biological sample.

10. The method of claim 9, wherein the biological sample is a tissue sample, serum, plasma, blood, dry blood spot, urine, saliva, sputum, tears, cerebrospinal fluid, seminal fluid, or feces.

11. The method of claim 9, wherein the one or more analytes are protein(s), lipid(s), carbohydrate(s), nucleotide(s), metabolite(s), vitamin(s), hormone(s), or steroid(s).

12. The method of claim 11, wherein the one or more analytes are ceramide and lyso-sphingomyelin, and the source sample is derived from the blood of a patient with acid sphingomyelinase deficiency.

13. The method of claim 12, wherein the ceramide and lyso-sphingomyelin are extracted from a blood sample with an extraction solvent comprising 80% methanol (v/v), 15-20% acetonitrile (v/v), 0-5% water (v/v), 10 mM ammonium acetate, and 1% formic acid.

14. The method of claim 12, wherein the first LC column is a silica column, and the second LC column is a C18 column.

15. The method of claim 14, wherein the solvent system comprises 0.5% trifluoroacetic acid.

16. The method of claim 14, wherein the solvent system applied to the first and second LC columns comprises 0-85% methanol (v/v), 0-15% acetonitrile (v/v), and 0-100% water (v/v).

17. The method of claim 16, wherein the solvent system is obtainable by mixing a first solvent comprising water and 0.5% trifluoroacetic acid, and a second solvent comprising 85% methanol (v/v), 15% acetonitrile (v/v), and 0.5% trifluoroacetic acid.

18. The method of claim 17, wherein the ratio of the first solvent to the second solvent is 70:30, 85:15, or 99:1.

* * * * *